United States Patent
Jonsson et al.

(10) Patent No.: US 7,187,183 B2
(45) Date of Patent: Mar. 6, 2007

(54) APPARATUS AND METHOD FOR MICROWAVE DETERMINATION OF AT LEAST ONE PHYSICAL PARAMETER OF A SUBSTANCE

(75) Inventors: Olafur H. Jonsson, Reykjavik (IS); Jon Thor Thorgeirsson, Bessastadahrepp (IS); Alan John Sangster, Edinburgh (GB)

(73) Assignee: Intelscan Orbylgjutaekni enf., Reykjavik (IS)

(*) Notice: Subject to any disclaimer, the term of this patent is extended or adjusted under 35 U.S.C. 154(b) by 0 days.

(21) Appl. No.: 10/479,324

(22) PCT Filed: May 31, 2002
(Under 37 CFR 1.47)

(86) PCT No.: PCT/IS02/00011

§ 371 (c)(1),
(2), (4) Date: Apr. 28, 2004

(87) PCT Pub. No.: WO02/097411

PCT Pub. Date: Dec. 5, 2002

(65) Prior Publication Data

US 2004/0239338 A1 Dec. 2, 2004

Related U.S. Application Data

(60) Provisional application No. 60/294,249, filed on May 31, 2001.

(30) Foreign Application Priority Data

May 31, 2001 (IS) .......................................... 5960

(51) Int. Cl.
*G01R 27/04* (2006.01)
(52) U.S. Cl. ...................... 324/642; 324/643; 324/644
(58) Field of Classification Search ........ 324/642–646, 324/631–632, 640
See application file for complete search history.

(56) References Cited

U.S. PATENT DOCUMENTS 3,247,508 A 4/1966 Bradford et al.
(Continued)

FOREIGN PATENT DOCUMENTS

SU 1506387 9/1989
(Continued)

OTHER PUBLICATIONS

International Search Report; PCT/IS02/00011; Aug. 28, 2002; Asa Malm.
Abstract; SU 1 223 028; Apr. 7, 1986.

*Primary Examiner*—Andrew H. Hirshfeld
*Assistant Examiner*—Marina Kramskaya
(74) *Attorney, Agent, or Firm*—Fish & Richardson P.C.

(57) ABSTRACT

A method and an apparatus is described to measure at least one physical parameter of a substance such as moisture and salt content. This is done by transmitting a microwave beam through the material to be measured and detect only a reflection of a predetermined polarity of the transmitted waves. To accomplish this a polarizing plate is used so that only cross-polarized microwaves, which pass through the substance are detected and the co-polar reflections from surrounding structures are excluded. The object can either be moving as on a conveyer belt or in a rest position.

23 Claims, 6 Drawing Sheets

U.S. PATENT DOCUMENTS

| | | | |
|---|---|---|---|
| 3,783,373 A | | 1/1974 | Jawor |
| 4,052,666 A | | 10/1977 | Fletcher et al. |
| 4,344,030 A | * | 8/1982 | Anderson et al. ............ 324/642 |
| 4,479,128 A | | 10/1984 | Brunner et al. |
| 4,599,623 A | * | 7/1986 | Havkin et al. ............... 343/756 |
| 4,707,652 A | * | 11/1987 | Lowitz ........................ 324/631 |
| 4,745,361 A | * | 5/1988 | Nees et al. .................. 324/753 |
| 4,757,514 A | | 7/1988 | Hoag |
| 4,818,930 A | * | 4/1989 | Flemming et al. ........... 324/631 |
| 4,947,128 A | * | 8/1990 | Hatton et al. ................ 324/640 |
| 5,315,258 A | * | 5/1994 | Jakkula et al. ............... 324/640 |
| 5,497,100 A | * | 3/1996 | Reiser et al. ................ 324/643 |
| 5,781,018 A | * | 7/1998 | Davidov et al. ............. 324/637 |
| 5,959,594 A | * | 9/1999 | Wu et al. .................... 343/909 |
| 6,100,703 A | * | 8/2000 | Davidov et al. ............. 324/631 |
| 6,163,158 A | * | 12/2000 | Moeller et al. .............. 324/633 |
| 6,172,510 B1 | * | 1/2001 | Liu ............................. 324/632 |
| 6,452,404 B2 | * | 9/2002 | Moeller et al. .............. 324/633 |
| 6,529,154 B1 | * | 3/2003 | Schramm et al. ............. 342/44 |
| 6,531,881 B1 | * | 3/2003 | Cordes et al. ............... 324/644 |

FOREIGN PATENT DOCUMENTS

| | | |
|---|---|---|
| WO | WO 8502266 | 5/1985 |
| WO | WO 0102841 | 1/2001 |
| WO | WO 0214847 | 2/2002 |

* cited by examiner

Upper line is the 12GHz frequency attenuation in the sample, and the lower line is the 8GHz frequency attenuation.

APPARATUS AND METHOD FOR MICROWAVE DETERMINATION OF AT LEAST ONE PHYSICAL PARAMETER OF A SUBSTANCE

This application claims priority from Icelandic application No. 5960 and U.S. provisional application No. 60/294,249, filed May 31, 2001.

FIELD OF THE INVENTION

The present invention concerns a method and apparatus for determining at least one physical parameter of an object by means of transmitting microwaves towards the object and analysing the co-polar and cross-polar transmitted and reflected microwaves.

BACKGROUND OF THE INVENTION

It is well known that during processing of a variety of products such as wood, tobacco and food the moisture content in the product plays an important role before the product enters the final stage in the production.

When the moisture content is measured by using microwave radiation, the microwaves interact with the water molecules in the substance being measured. Due to the dipole character of the water molecule, the microwave fields interact with the molecules resulting in a rotational and translational motion of the molecules causing heat absorption of the incident energy. By measuring the attenuation (loss of energy) of the microwaves along with the phase shift (loss of velocity) of the microwaves the moisture content of the material can be accurately determined. This is typically done by transforming the output signal to an electrical signal. The attenuation and phase shift within a material can be used to calculate the dielectric properties of that material. The dielectric properties of a material are usually expressed by the relative complex permittivity, $\epsilon=\epsilon'+j\epsilon''$, where $\epsilon'$ is the dielectric constant that represents the ability of a material to store electric energy, and $\epsilon''$ is the loss factor representing the loss of electric field energy in the material. By knowing both $\epsilon'$ and $\epsilon''$ one can calculate water content and density of the material according to published formulae.

Furthermore, other physical parameters such as fat, protein and salt can be determined, for example by using more than one frequency and isolating the absorption effects due to water and absorption due to the presence of salt ions, which are governed by the difference in the frequency dependence of the two loss mechanisms. By doing repeated analysis with the device and by comparing results obtained by using conventional methods, calibration can be achieved.

Hitherto known methods using microwaves generally only measure moisture content but not other physical parameters such as fat, protein and salt. For example, no device has been made to measure fat content using non-contact microwave techniques. A hand held device has been made that estimates fat content using microwaves. However, the device needs to be in firm contact with the substance to be measured and actually measures the moisture content. The device is precalibrated and calculates the fat content from the measured moisture content.

Other systems and methods have been developed for measuring the moisture content of material. One is to use a hand held instrument, similar to the one mentioned above, a so called "stripline" sensor. The instrument is placed on the material in such a way that the stripline is in close contact with the material. Microwaves are then generated and fed along the stripline, and the attenuation is measured in the stripline. The attenuation or loss is then converted to water content. This method is a surface measurement. To obtain overall moisture content in bulk material, it is necessary to measure at several places, and turn the object around. The average value is then used as an indicator.

In another device the material is placed between the transmitting and receiving antennas of a microwave transmission system and by comparing the output signal from the material with the source signal the material properties can be deduced.

In U.S. Pat. No. 4,578,998, there is disclosed a microwave system using different polarization of signals. Two radiators are used to measure across a sheet material by utilizing two different polarizations so that signal interchange between them is avoided. The polarization is in other words used to distinguish between radiators.

The problem with the disclosure of U.S. Pat. No. 4,578,998 is that the measured signal comprises both the attenuation through the material and also reflections from microwaves bouncing off surrounding material, which is not being examined. This will introduce errors into the result.

The disadvantage of using the hand held contacting instrument is that it is a surface measurement of a bulk material. Therefore it is time consuming to obtain a measurement for the material as a whole due to the fact that one has to measure on various spots around the material and also due to the inconvenience of having a human operating the instrument by placing the sensor in contact with the material while measuring it. This can cause errors since people will never operate the instrument in exactly the same way.

GENERAL DESCRIPTION OF THE INVENTION

It is an object of the present invention to improve the above mentioned methods by providing a method and an apparatus to measure at least one physical parameter of a substance, such as moisture and fat content of bulk material. This is done by utilizing the polarization to create a transmission path through the sample, wherein a microwave beam is transmitted through the material to be measured and only a reflection of a predetermined polarity of the transmitted waves is detected. This has the advantage that only the signal that has traveled through the material is measured. This is accomplished by providing a polarizing plate so that only cross-polarized microwaves, which pass through the substance, are detected and co-polar reflections from surrounding structures are excluded. This increases therefore the sensitivity and accuracy of the measurement. Accordingly, only those waves are received that have bounced off the polarizing plate after passing through the substance being measured. When the system is set up to detect cross-polar reflections it can be ensured that the measured microwaves have passed through the object twice before being detected. When the system is set up to detect co-polar reflections the distance of the surface of the material from the aperture of the receiver antenna can be determined and this can be related to the depth of the material by comparing with co-polar reflections when no material is present.

The first aspect of the present invention relates to an apparatus for determining at least one physical parameter of an object by means of transmitting microwaves towards the object and analyzing the reflected microwaves, said apparatus comprising:

a source for generating a time dependent electrical signals, a transmitter positioned in proximity to the object for converting the time-dependent electrical signals to microwaves and transmitting the microwaves towards the object, a polarizer positioned adjacent to the object and opposite to the transmitter for rotating at least part of the polarization of the transmitted waves and reflecting a predetermined polarity of the transmitted waves, a receiver positioned opposite to the object with respect to the polarizer for receiving the reflected microwaves of predetermined polarity and converting them into an electrical signal, and a computer system for utilizing the electrical signal for calculating the at least one physical parameter of the object.

Further, control electronics are preferably provided to control the source. The polarizer may be a plate with a plurality of parallel metallic wires positioned in the horizontal plane of the polarization plate for rotating at least a part of the transmitted waves. These wires can be supported by a non-reflecting medium such as a plastic material. The bottom layer of the polarization plate is a reflecting material such as a metallic plate. As the microwaves hits the polarization plate part of them hits the wires that rotate the polarization and a part passes between the wires through the supporting material until it is reflected from the bottom plate. The bottom plate reflects the microwaves according to the law of reflection, wherein a part of these reflected microwaves hit the wires that rotate the polarization. With a proper thickness of the polarization plate, i.e. interval between the wires and the bottom plate, the "second" polarization can be the same as the "first" polarization. Preferably, this interval is $\frac{1}{4}\lambda$(lambda), where $\lambda$ is the wavelength of the microwaves, or generally $(\frac{1}{4}+n)\lambda$ with n as an integer. This is however typically the case when air is between the wires and the reflecting plate. However, this thickness ratio is different when there is a material between the wires and the reflecting plate, and depends on the dielectric properties of the material. The rotated polarization is received with a receiver that converts the microwaves to an electrical signal. This polarization of this received microwave can for example be 90° rotated with respect to the transmitted microwaves, which can be linearly polarized and/or circular polarized. The receiver can for example be an antenna or a dipole.

The frequency of the time-dependent electrical source signal depends on whether only one parameter is measured, such as moisture, or more parameters are measured, such as moisture and salinity. This is due to the different characteristic of the water and salinity molecules and their resonance frequency. In one embodiment the time dependent electrical signal has a frequency in a sequential cyclic, i.e. first the frequency is for measuring the moisture and the second, different frequency, is for measuring the salinity. Therefore the time-dependent electromagnetic field has at least one frequency.

For determining at least one physical parameter of the object, which can be the moisture content and/or the density of the object, it may be useful to use a reference channel. In one embodiment the apparatus is provided with a coupler for dividing the electrical signal between the transmitter which can be a transmitting antenna and the receiver, wherein the part of the electrical signal directed towards the receiver passes trough a reference channel and is used as a reference signal. Preferably half of the source signal passes through the reference channel and the other half to the transmitting antenna.

The measurements on the object can be as the object is in a rest position or as the object is being conveyed by a conveying means such as a conveyor belt. The transmitting and the receiving antennas will normally be in close proximity at a suitable position above the object with their radiation patterns directed at the object. For attenuation measurements the antennas are with respect to each other orthogonally polarized.

Furthermore, to measure the permittivity constant of the material, it is important to be able to determine the thickness of the material. One way of measuring this is by implementing a second receiving antenna positioned above to the object with respect to the polarizer and close to the transmitting antenna. The co-polar signal therefore measures the difference in distance when no material is present and when material is present. Preferably, the polarity of the received microwave is in this case the same as of the transmitting microwaves. It is also possible to use ultrasound for the same purpose.

A further aspect of the present invention is to provide a method for determining at least one physical parameter of an object by means of transmitting a microwave towards the object and measuring the reflection, said method comprising the steps of:

generating a time-dependent first electrical signal and converting at least part of the first electrical signal to microwaves, transmitting the microwaves towards the object, reflecting the transmitted microwaves by a polarizer positioned adjacent to the object and opposite the transmitter wherein at least part of the polarization of the reflecting microwaves is rotated, receiving the rotated part of the reflected microwaves from the polarizer with a receiver positioned opposite to the object and converting the received part of the transmitted wave into an second electrical signal, and analysing the second electrical signal and determining at least one physical parameter.

In one embodiments the time-dependent electrical signal from the source is split in two, partly passing through a reference channel and partly passing from the polarizing plate to a receiving means, and thereafter the two signals are added again. The summed signal is used as a reference signal with a reference phase and a reference level, for example when no material is present on the polarizing plate. Any deviation from this reference phase and reference level when an object is placed on the polarizer is used to determine relative complex permittivity of the object. A shift in the reference phase or frequency can be used to calculate the dielectric constant $\epsilon'$, and a shift in the reference level can be used to calculate the loss factor $\epsilon''$ of the object. Another parameter which is important when calculating $\epsilon'$ and $\epsilon''$ is thickness of material which microwaves travel through. This parameter can be determined for example by using a second receiving means positioned opposite to the object with respect to the polarizer. The second receiving means would preferably be adjusted so that it detects microwaves of the same polarity as the transmitted microwaves. Therefore the part of the microwaves that is reflected from the object is determined and compared to a reference signal, for example a signal without any object, and the phase shift from this reference signal is used to determine the height of the object. By knowing the distance between the aperture and the polarizing plate, and the angle of radiation from the transmitting horn, the effective measurement area can be determined. Together with the thickness, the volume is thus calculated.

The transmitted microwaves can be linear polarized and the polarization part of the reflected wave that the receiving means detects is preferably 900 polarized with respect to the transmitted microwave. This is to ensure that only the part of the transmitted waves which have passed through the entire object is detected, wherein the polarizer is located under the object and therefore the microwaves with this polarization must pass through the object. One way of measuring the phase change and attenuation change in a material is by using a reference channel. The sum of the signal from the reference channel and the signal reflecting of the polarizer, will be zero, with the aid of an adjustable attenuator and phase shifter in the reference channel when no material is present. Rather than using linear polarization of the microwaves it may be possible to use circular polarization, for example in cases where fibres in the material are likely to be predominantly in one direction, for example perpendicular to the transmitting angle.

Furthermore, the moisture content can be used to determine the fat concentration of an object such as fish, where the buoyancy is known and constant, and therefore the relationship between fat and water in the body is established by an empirical formula. This could be achieved by using historical data.

DETAILED DESCRIPTION

In the following, the present invention, and particular preferred embodiments thereof, will be described in greater details in connection with the accompanying drawings in which, FIG. 1 is a flow chart showing how one embodiment can be used with the method of the present invention to measure moisture content.

Figure 1:
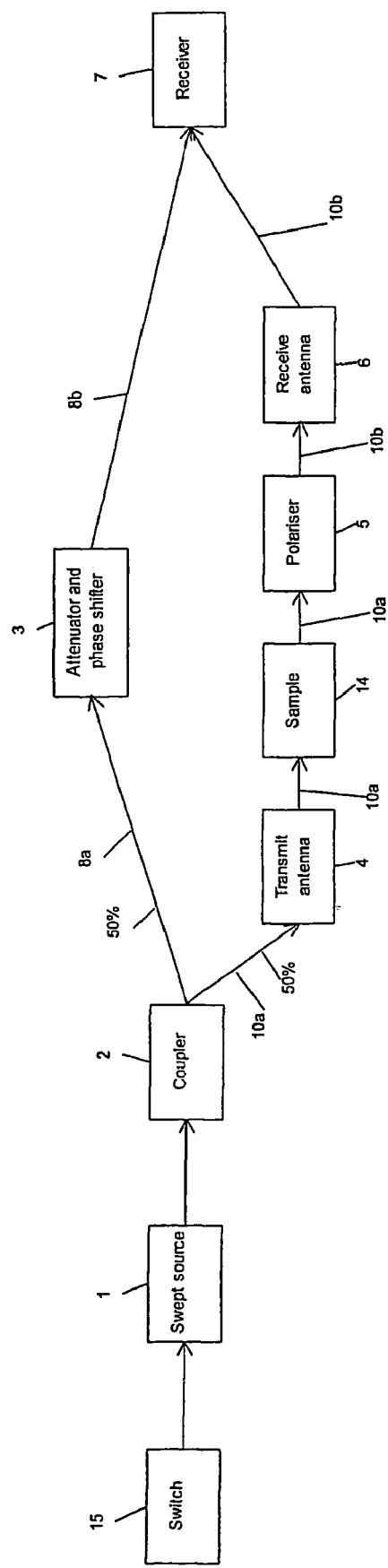

FIG. 1 is a flow chart showing how one embodiment of the apparatus can be used with the method of the present invention to measure moisture content. The apparatus includes a microwave radiation source 1, shown to the left of the coupler 2. In a preferred embodiment the microwave radiation source 1 is a swept source that sequentially transmits microwaves with a frequency which changes preferably linearly with time over a specified frequency bandwidth. The source (or sources) may be arranged to transmit more than one centre frequency. The swept source 1 receives a signal from the switch 15 before sending a signal to the coupler 2. The switch 15 determines which centre frequency is transmitted.

The signal from the swept source 1, once amplified to an appropriate level, is then divided at the coupler 2, with part of the signal passing through a reference channel to the receiver 7, while the remaining signal passes to the transmitter antenna 4 in the measurement channel. Preferably, the signals that go to the two different directions are equal, each part being exactly 50% of the original signal.

It will be appreciated that the sample being measured can be replaced with a continuous flow of bulk material without departing from the principles of the present invention. For the purpose of this illustration the apparatus will be described only with a single sample to be measured.

The microwaves are directed at the sample by means such as transmitting antenna 4. Alternatively, a planar antenna can be used for the same purpose. The source signal 10a is a very high frequency microwave signal which is frequency modulated by linearly sweeping the source oscillator from a frequency just below the centre frequency to a frequency just above it over a predetermined bandwidth. The preferred centre frequency for the source signal depends on the nature of the sample 14 and the number of frequencies depends on the number of physical parameters to be measured, such as moisture, salt or protein.

The source signal 10a is a very high frequency microwave signal which is frequency modulated by linearly sweeping the source oscillator from a frequency just below the centre frequency to a frequency just above it over a predetermined bandwidth. The preferred centre frequency for the source signal depends on the nature of the sample 14 and the number of frequencies depends on the number of physical parameters to be measured, such as moisture, salt or protein.

The source signal 10a passes through the sample 14, hits the polarizer 5 and is reflected back. As the source signal 10a has passed through the sample it is both attenuated and slowed. The extent of this attenuation is determined mostly by the loss factor $\epsilon''$ of the material of the sample 14 encountered by the source signal. The degree to which the source signal is slowed is predominantly determined by the dielectric constant $\epsilon'$ of the material 14.

As the source signal 10a hits the polarizer 5 the polarizer 5 changes the polarization of the signal to that of the receiver antenna 6. The transmitter antenna 4 and the receiver antenna 6 are essentially identical except that they will be orthogonally polarized. This means that any reflections off the sample, conveyer belt or conveyer belt superstructure or any surroundings, plus any direct radiation from the transmitter antenna 4 to the receiver antenna 6, will not be identified by the receiver 7 since these signals will not have the correct polarization for entry into the receiver antenna 6. Once the system is calibrated the receiver 7 will detect, in principle, only those electrical changes in the measurement signal due to the presence of a sample 14 in the system. The sample 14 will introduce additional phase shift and attenuation in the measurement channel. In a preferred embodiment, there is only one receiving antenna but it will be appreciated that there can be more than one receiving antenna.

In one embodiment, a frequency mixer is used in both reference and measurement channels to measure the phase difference. In another embodiment, the reference signal 8a goes to an attenuator and phase shifter 3. The attenuator and phase shifter 3 will be set during calibration so that this channel replicates the electrical characteristics of the measurement channel in the absence of a sample 14 or in the presence of a sample of known characteristics.

The receiver 7 adds the reference signal 8b and the measuring signal 10b in anti-phase at the receiver input. The inserted phase shift and the attenuation in the reference channel which produces a null signal at the receiver is recorded. The recorded phase shift and the attenuation are sent to the processor where the calculation of physical parameters such as moisture is done.

In an apparatus where more than one frequency is used, the method is the same as above and the switch 15 then switches between different frequencies.

The description above is a description of one embodiment. Generally there are four main ways to perform the measurement:

1. The simplest embodiment would be to use a swept oscillator 1 together with both an electrically controllable (programmable) phase shifter and attenuator 3 in the reference channel. In this embodiment the receiver controlled phase shifter and attenuator 3 are adjusted until the added signals at the receiver input are in 'exact' antiphase producing a 'null' input signal 4 in FIG. 4, at the calibration frequency. The recorded change in both attenuation and phase shift when sample 14 is present is sent to the processor.
2. The source 1 is un-swept but frequency controllable and the reference channel contains only an electrically controllable attenuator 3. In this case the oscillator frequency and the attenuator 3 are adjusted to produce a null at the receiver 7. The recorded change in frequency and attenuation are passed to the processor.
3. A swept frequency source 3 is used, which permits the frequency responses shown in FIG. 4 to be produced at the receiver. The receiver electronics are more complicated and are required to be able to record the change in shape of this response, which is an indication of the phase change and attenuation change due to the substance being measured. In this case the reference channel's programmable phase shifter and attenuator are not needed since the more sophisticated electronics are providing the requisite phase shift and attenuation information. However, the manually adjusted attenuator and phase shifter 17 in FIG. 3 will still be present to calibrate the system to achieve an exact antiphase or null input signal 26 in FIG. 4, at a certain frequency, when no sample is present.
4. The source 1 is unswept, and both the attenuation change and the phase shift change caused by the insertion of a sample, are determined directly through separate cross-polar receiver channels, one for amplitude and the other for phase. In the amplitude channel, a rectifying diode is used to provide a d.c. signal level which is a measure of the sample attenuation. In the phase channel, a double-balanced frequency mixer is used to provide an I.F. (d.c.) signal level which is a measure of the phase change caused by the sample.

Figure 2A:
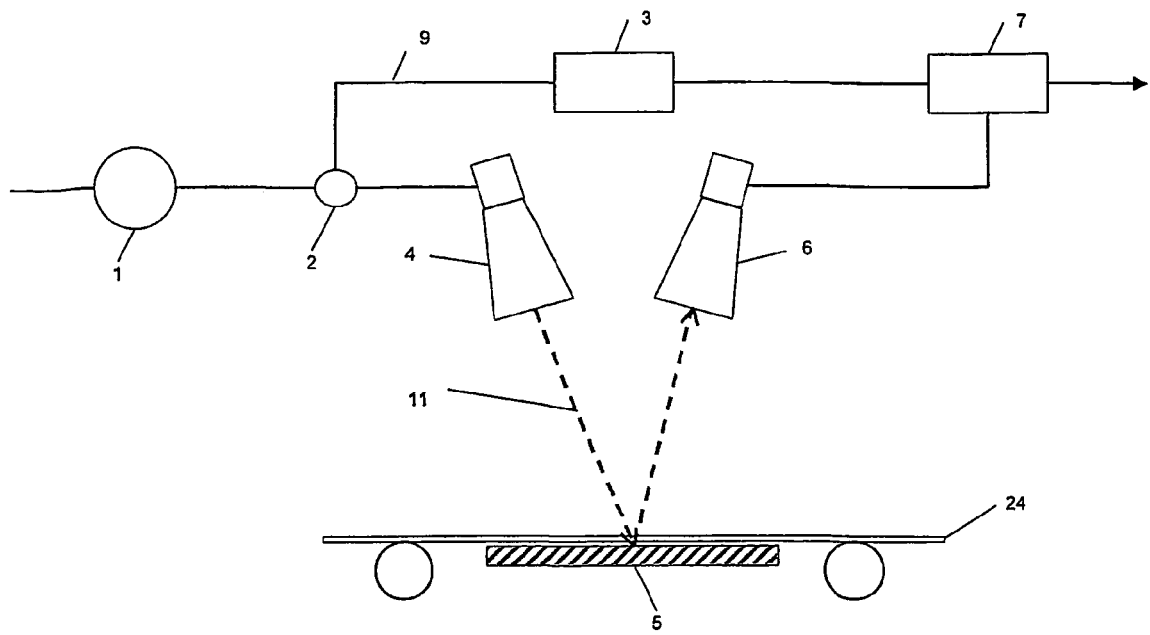
FIGS. 2a and 2b are schematic drawings of one embodiment of an apparatus, which can be used with the method of the present invention.
Figure 2B:
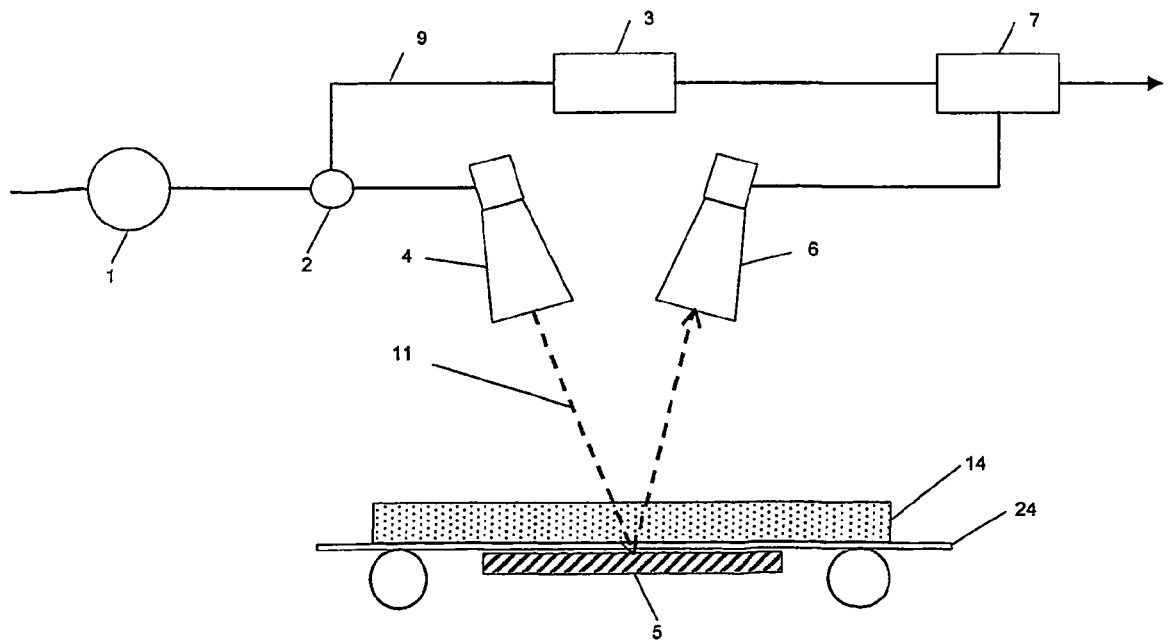

FIGS. 2a and 2b are schematic drawings of one embodiment of the present invention demonstrating a very simple version of an apparatus. The microwave source 1, which can be a swept sources generates a timed dependent electrical signal, where a part of the signal is divided at the coupler 2 where part of the signal is used as reference signal 9, while the remaining signal passes to the transmitter antenna 4 where part of it is reflected from the polarizer 5 and going through the object 14. This is called the measurement signal 11.

Figure 3:
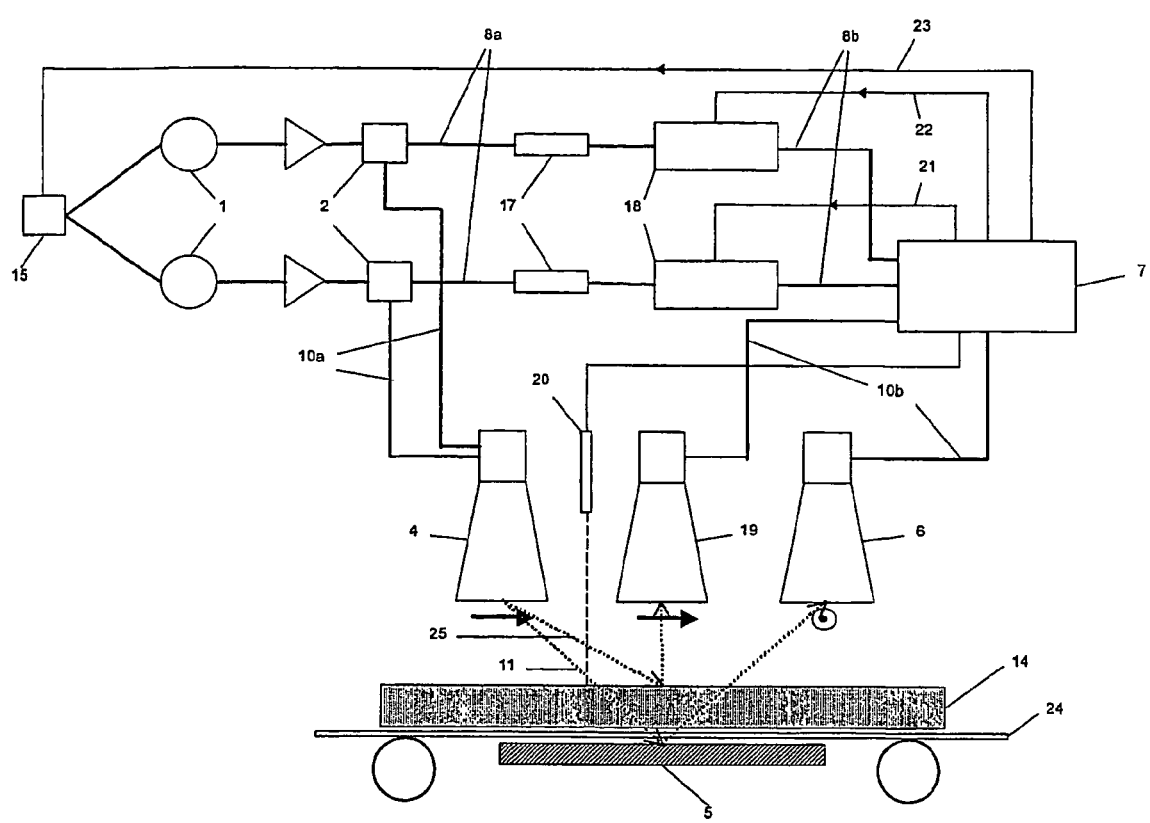
FIG. 3 is a schematic drawing of a second embodiment that can be used with the present invention for measuring moisture content. Furthermore, this embodiment also measures the depth and hence the density of the object or substance being measured.

FIG. 3 is a schematic drawing of a second exemplary embodiment of an apparatus that can be used with the present invention. This apparatus measures similar to the apparatus in FIG. 2 the moisture and salt content of a sample (tobacco), wherein the sample can be in a rest position or being conveyed on a conveyor belt.

This apparatus uses two frequencies since it is measuring two different physical parameters, moisture and salt content. Therefore the switch 15 switches between 8 GHz and 12 GHz after receiving a signal from the receiver 7. Other frequencies can be used for the same results.

The apparatus includes a microwave radiation source 1. The swept source 1 receives a signal from the switch 15 before sending a signal to the coupler 2. The signal from the swept source 1, once amplified to an appropriate level, is then divided at the coupler 2, with part going as a reference signal 8a through a reference channel to the receiver 7, while the remaining signal passes to the transmitter antenna 4 as the measurement signal 10a. The signals that go to the two different direction are ideally equal, each part being exactly 50% of the original signal.

The microwaves are directed at the sample and are transmitted from the transmitter antenna 4. The source 1 is a very high frequency microwave oscillator the frequency of which is changed linearly with time in a repetitive manner over a prescribed bandwidth.

A part of the transmitted signal 11 passes through the sample 14, hits the polarizer and is reflected back. Another part of the transmitted signal 25 is reflected as the signal hits the sample. That part is received by the co-polarized receive antenna 19 and is used to measure the thickness of the sample 14 by detecting the phase shift of the first reflection. The part that passes through the sample 14 and hits the polarizer is received, after reflection and change in polarization, by the transverse polarized receive antenna 6.

The reference signal 8a goes to a manually adjusted attenuator and phase shifter 17 and then to a programmable/variable attenuator and phase shifter 18. The manually adjusted attenuator and phase shifter 17 is used to calibrate the signal once the apparatus is set up so as the summed signal is 0 at a certain frequency in the frequency sweep, when there is no object present. When a sample is present, it increases the attenuation and phase shift in the microwaves in the measurement channel and the signal 10b is weaker as it goes into antenna 6. Receiver 7 then sends a signal to adjust the programmable/variable attenuator and phase shifter 18 to achieve a summed signal of null again. The amount of adjustments is recorded as the measurement values of attenuation and phase of the sample.

An infrared thermometer 20 measures the temperature of the sample 14 and sends a signal to the receiver so that measurements of the relative complex permittivity can be corrected for different temperatures.

The receiver 7 adds the reference signal 8b and the measuring signal 10b in anti-phase. When phase shift and attenuation 18 is adjusted correctly, a null is detected, meaning that attenuation in 8b is the same as in 10b. The phase shift and the attenuation in the reference channel are then recorded. The detected phase shift and the attenuation is sent to the processor where the calculation and conversion of values into meaningful information is done.

Figure 4:
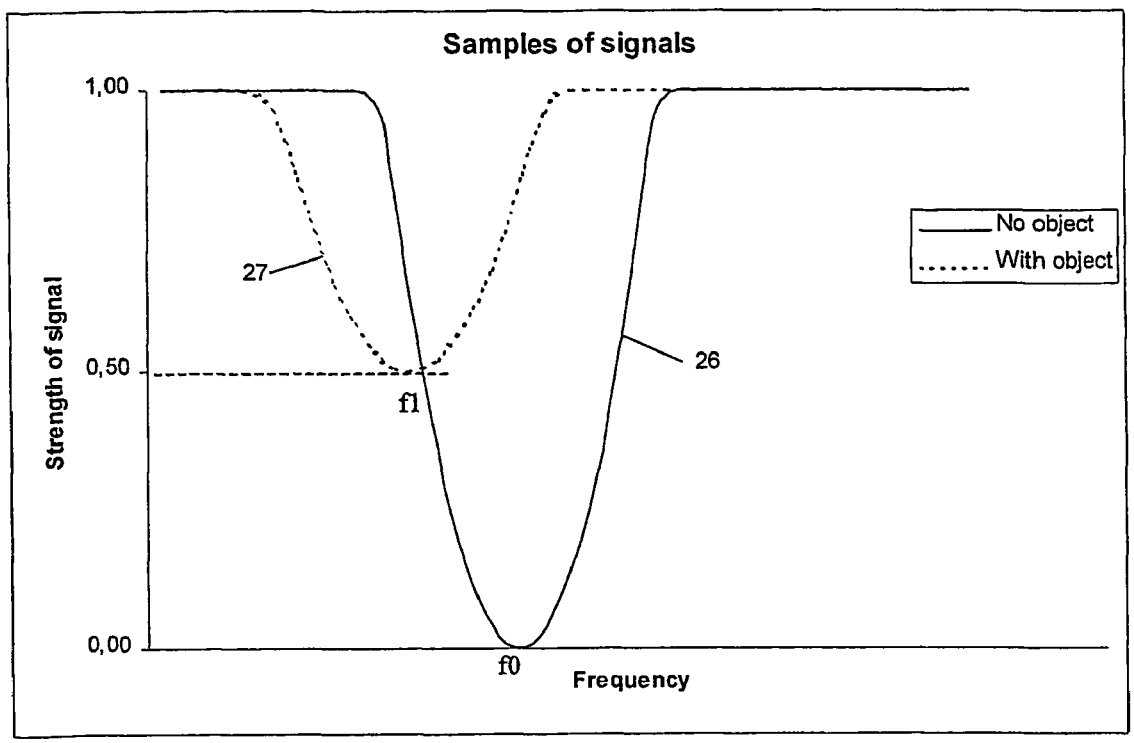
FIG. 4 is a graph showing samples of the electrical response to the presence of an object or substance within the transmitted beam, which is used to calculate the density of the measured object and the wet mass of the measured object.

FIG. 4 is a graph showing an example of an electrical signal from receiver 7 used to calculate the $\epsilon'$ and $\epsilon''$ of a sample. The x-axis represents the frequency sweep of the source and the y-axis shows the strength of the signal. At first, no sample is present and the system is tuned to give response 26. When sample is present, attenuation of transmitted microwaves increases due to loss in the material, and there will be a phase change. Since the signal is unchanged in the reference channel, the sum of the reference signal and the measurement signal changes when sample is present, and this is shown by response curve 27. The difference in horizontal direction represents phase change and difference in vertical direction represents attenuation change due to the sample, and these parameters are used to calculate $\epsilon'$ and $\epsilon''$ according to published formulae.

Both the wet-mass and the density determination can be based on historic data depending on the object, which can for example be e-tobacco, wood or corn. Each of these objects may have their own relation between the phase shift and attenuation and the actual moisture content and density. Rather than using formulae, one could choose to collect data from the apparatus and fit to the actual values of moisture and density.

In FIG. 4 the curve 26 shows a measured signal when there is no sample being measured, as in FIG. 2a. In this case the measured signal is the same as the reference signal, but with different polarization. Thus, the sum of the reference signal and the measured signal is then 0 at a certain frequency in the sweep. The reference value is then 0 for no moisture present.

The measuring curve 27 shows when the signal goes through a sample with moisture. In this case the sample reduces or attenuates the signal by 50%. Since the reference signal is unchanged, the sum of the reference signal and the measured signal is changed by 50% in the vertical direction, which is the attenuation axis. If the sample was pure water, absorbing all microwaves, measurement signal would be attenuated to nothing, and only reference signal would be received, giving a straight line at the attenuation level of the reference signal.

Furthermore, the curve 27 represents a phase shift in the microwaves for a frequency sweep, which can be seen by the location of the minima of the signal, which has moved to the left from $f_0$ to $f_1$. This phase shift is as mentioned before used to calculate the density of the sample.

From calculating density by using the relative complex permittivity, using the formula for density $\rho=(m_{wet}+m^{dry})/V$ and by knowing the wet mass $m_{wet}$ the dry mass can be calculated if the volume of the object is known. As shown in FIG. 3, the volume can be estimated by means of using the co-polarized receive antenna 19 to measure the thickness of the sample 14, which can be registered periodically. If the object is being transported on a conveyer belt with a constant speed, the object can be divided into parts with a fixed height and different thickness.

Figure 5:
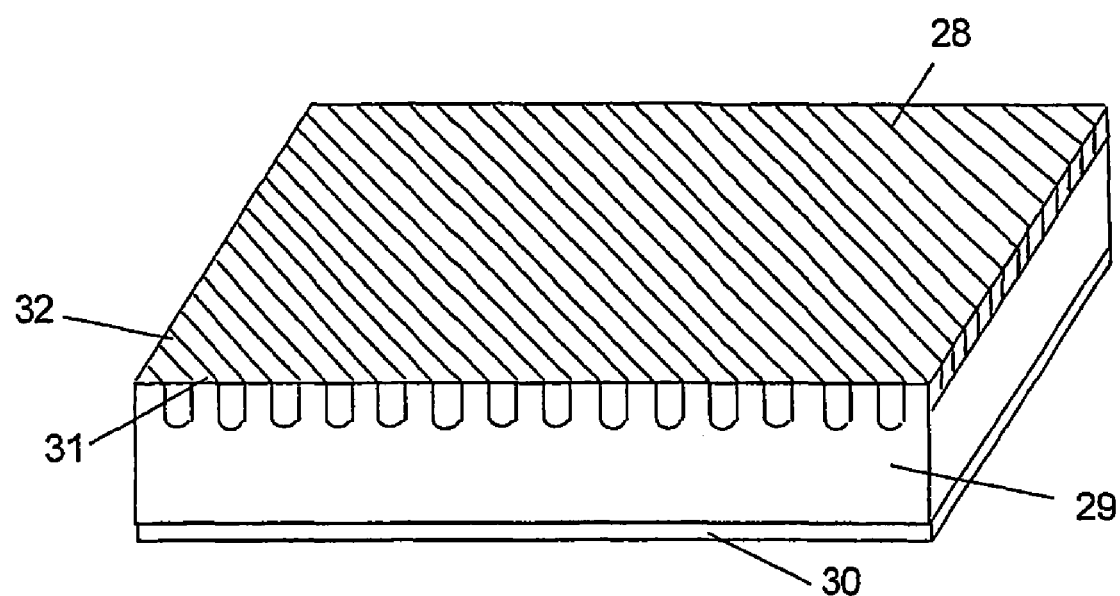
FIG. 5 shows one embodiment of the polarizer.

FIG. 5 shows one embodiment of the polarizer, comprised of parallel metallic wires 28 positioned in the horizontal plane of the polarization plate for rotating at least a part of the transmitted waves. These wires can be supported by a non-reflecting medium 29 such as a plastic material. The bottom layer of the polarization plate can be a reflecting material such as a metallic plate 30. As the microwaves hits the polarization plate part of them hits the wires that rotate the polarization and a part passes between the wires through the supporting material until it is reflected from the bottom plate 30. Having the side of the polarization plate positioned parallel to the line between the transmitter antenna 4 and the receive antenna 6 and the two 45° angles 31, 32 equal ensures a 90° rotation in the polarization of both the incoming microwaves from the transmitter antenna 4 and the microwaves reflected from the bottom plate 30 that hit the metallic wires 28 on the way out of the non reflected medium 29.

The invention is further illustrated by the following example, which is not intended to be limiting in any way.

EXAMPLE

Figure 6:
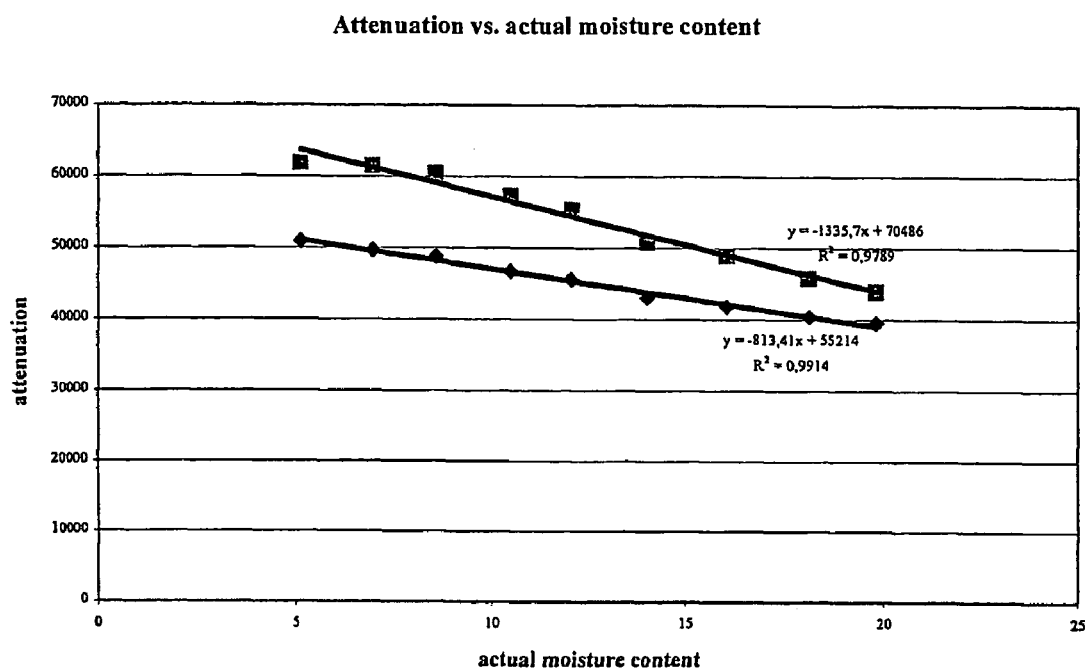
FIG. 6 shows results from experiments with the apparatus

The following example is based on an experiment carried out on 9 samples of tea leaves, where each sample was around 100 g, and each with different moisture content, from 5% moisture to 20% moisture. Two swept frequencies were used, one around 8 GHz and one around 12 GHz. Attenuation was measured in the samples, but not the phase change. The experiment shows a linear relationship between attenuation and actual moisture content of the sample, as can be seen in FIG. 6. The correlation coefficient was high; 0.9914 for the 8 GHz frequency and 0.9789 for the 12 GHz frequency. The correlation coefficient is a factor from 0 to 1, which represents how well the data points fall on to a fitted line.

The invention claimed is:

1. An apparatus for measuring at least one physical parameter of an object by means of transmitting microwaves towards the object and analyzing microwaves that have passed through the object, said apparatus comprising:
    source for generating time dependent electrical signals,
    a transmitter positioned in proximity to the object for converting the time dependent electrical signals to microwaves and transmitting the microwaves towards the object,
    a polarizer positioned adjacent to the object and opposite to the transmitter for rotating at least part of the polarization of the waves transmitted through the object and reflecting a predetermined polarity of the transmitted waves,
    a receiver positioned opposite to the object with respect to the polarizer for receiving the reflected microwaves of predetermined polarity that have passed through the object twice and converting them into an electrical signal,
    wherein said transmitter and said receiver are orthogonally polarized with respect to each other,
    a computer system for utilizing the electrical signal for calculating the at least one physical parameter of the object.

2. An apparatus according to claim 1, further comprising control electronics for controlling the source.

3. An apparatus according to claim 1, wherein the polarizer is a plate with a plurality of parallel wires positioned in a horizontal plane of the plate for rotating at least a part of the transmitted waves.

4. An apparatus according to claim 1, wherein the thickness of the polarizer is ¼ the wavelength of the microwave.

5. An apparatus according to claim 1, further comprising a coupler for dividing the electrical signal between the transmitter and the receiver, wherein the part of the electrical signal to the receiver passes through a reference channel and is used as a reference signal.

6. An apparatus according to claim 1, wherein the object is being conveyed as the object is being measured.

7. An apparatus according to claim 1 wherein said at least one physical parameter is the moisture content and/or the density of the object.

8. An apparatus according to claim 1, wherein the receiver is an antenna.

9. An apparatus according to claim 1, wherein the receiver is a diode.

10. An apparatus according to claim 1, wherein the polarization of the transmitting microwaves is linear.

11. An apparatus according to claim 1, wherein the polarization of the transmitting microwaves is circular.

12. An apparatus according to claim 1, further comprising a second receiver positioned opposite to the object with respect to the polarizer for receiving at least part of the reflected microwaves.

13. A method for determining at least one physical parameter of an object by means of transmitting a microwave towards the object and measuring the reflection of waves that have passed through the object twice, said method comprising the steps of:

generating a time-dependent first electrical signal and converting at least part of the first electrical signal to polarized microwaves, transmitting said polarized microwaves towards the object, reflecting the transmitted microwaves by a polarizer positioned adjacent to the object and opposite the transmitter wherein at least part of the polarization of the reflected microwaves is rotated, receiving the rotated part of the reflected microwaves from the polarizer that have passed through the object twice with a polarized receiver positioned opposite to the object and converting the received part of the transmitted wave into a second electrical signal, the receiver being cross-polarized with respect to the transmitter, and outputting the second electrical signal for analysis and determination of at least one physical parameter.

14. A method according to claim 13, wherein a part of the first electrical signal is passed through a reference channel to the receiving means and is used as a reference signal.

15. A method according to claim 13, wherein the sum of the second electrical signal and the reference signal is used for determining at least one physical parameter.

16. A method according to claim 13, further comprising a second receiving means positioned opposite to the object with respect to the polarizer for receiving at least part of the reflected microwaves of predetermined polarity, wherein the received microwaves are converted into an electrical signal and wherein the phase shift of the electrical signal with respect to a reference signal is used to determine the height of the object.

17. A method according to claim 13, wherein the attenuation level and the phase shift of the second electrical signal is used to calculate the dielectric constant and the loss factor of the object.

18. A method according to claim 17, wherein the dielectric constant and the loss factor of the object are used to calculate the density of the object.

19. A method according to claim 17, wherein the dielectric constant and the loss factor of the object are used to calculate the moisture content of the object.

20. A method according to claim 16, wherein the volume, the density and the moisture content of the object are used to determine weight of the dry mass of the object.

21. A method according to claim 13, wherein the determination of at least one physical parameter of an object is based on historical data.

22. A method according to claim 13, wherein at a part of the generated microwaves and a part of the received rotated part of the reflected microwaves from the polarizer are fed to a frequency mixer to determine the phase shift between the generated microwaves and the reflected microwaves caused by the object.

23. A method according to claim 13, wherein the at least one physical parameter includes one or more of fat content, salt content, and protein content of said object.

* * * * *